United States Patent [19]

Kalopissis et al.

[11] Patent Number: 4,545,978
[45] Date of Patent: Oct. 8, 1985

[54] HAIR-DYEING PROCESS INVOLVING PROTECTION OF THE SCALP

[75] Inventors: Gregoire Kalopissis, Neuilly-sur-Seine; Jacqueline Gallien, Aulnay-sous-Bois; Bernard Jacquet, Antony; Daniel Bauer, Le Raincy; Jean Phillipe Chalaye, Maisons Alfort, all of France

[73] Assignee: L'Oreal, Paris, France

[21] Appl. No.: 508,010

[22] Filed: Jun. 27, 1983

Related U.S. Application Data

[62] Division of Ser. No. 214,864, Dec. 9, 1980, Pat. No. 4,402,698.

[30] Foreign Application Priority Data

Dec. 13, 1979 [LU] Luxembourg ............................ 81994
Jul. 30, 1980 [LU] Luxembourg ............................ 82581

[51] Int. Cl.$^4$ ..................... A61K 33/44; A61K 47/00; A61K 7/13
[52] U.S. Cl. ...................................... 424/10; 424/125; 514/770; 8/405
[58] Field of Search ........................ 424/10, 125, 357

[56] References Cited

U.S. PATENT DOCUMENTS

| 202,246 | 4/1878 | Delisser | 424/125 |
|---|---|---|---|
| 1,564,378 | 12/1925 | Stein et al. | 8/405 |
| 1,888,883 | 11/1932 | Norris | 8/405 |
| 2,009,394 | 7/1935 | Fiedler | 424/362 |
| 2,306,887 | 12/1942 | Klose | 424/2 |
| 2,365,705 | 12/1944 | Jeri | 427/154 |
| 3,193,465 | 7/1965 | Frowde | 8/405 |
| 3,708,435 | 1/1973 | Starkman | 424/357 |
| 3,775,044 | 11/1973 | Schrader | 8/11 |
| 3,884,627 | 5/1975 | Brody et al. | 8/10 |
| 4,268,264 | 5/1981 | Grollier et al. | 8/410 |
| 4,362,715 | 12/1982 | Strianse et al. | 424/357 |

FOREIGN PATENT DOCUMENTS

| 895838 | 3/1972 | Canada | 424/125 |
|---|---|---|---|
| 2451918 | 5/1976 | Fed. Rep. of Germany | 424/357 |
| 2910473 | 9/1979 | Fed. Rep. of Germany | 424/357 |
| 979294 | 1/1965 | United Kingdom . | |
| 2065177 | 6/1981 | United Kingdom | 8/405 |

OTHER PUBLICATIONS

The Merck Index, 8th ed., (Various pages), 1968.
The Merck Index, 9th Edition, 4217, p. 564.

*Primary Examiner*—Albert T. Meyers
*Assistant Examiner*—John M. Kilcoyne
*Attorney, Agent, or Firm*—Fleit, Jacobson, Cohn & Price

[57] ABSTRACT

A process is described which consists, in a first stage, in applying a composition based on a substance of vegetable or animal origin, a synthetic organic substance or a mineral substance, in suspension or in solution in a solvent and having a viscosity suitable for application to the hair, or as a powder, and making it possible to prevent or substantially to limit the passage of the dyestuffs and/or of the dyestuff precursors as far as the scalp, and, in a second stage, in dyeing the hair using one or more compositions, at least one of which contains either an oxidizable dyestuff or a direct dyestuff, the dyeing being followed, after an interval sufficient for coloring the hair, by rinsing and optionally by shampooing.

3 Claims, No Drawings

HAIR-DYEING PROCESS INVOLVING PROTECTION OF THE SCALP

This is a divisional of application Ser. No. 214,864 filed Dec. 9, 1980 now U.S. Pat. No. 4,402,698.

The present invention relates to a process for dyeing human hair.

In the dyeing of keratin fibres, and in particular human hair, a distinction is drawn between essentially two types of colouration, namely permanent colouration and semi-permanent or direct colouration.

Permanent colouration is carried out by applying a dyeing composition containing one or more so-called oxidation dyestuff precursors and an oxidising agent which is added to the composition just before application, or by applying directly a composition without an oxidising agent, if the composition contains one or more so-called rapid oxidation dyestuffs or certain diphenylamines; in the latter case, the development of the colour is caused by the oxygen in the air.

The term "oxidation dyestuff" refers to aromatic compounds of the diamine, aminophenol or phenol type, which are not dyestuffs in themselves but which are converted to dyestuffs by an oxidative condensation process. Amongst these oxidation dyestuffs, a distinction is generally drawn between, on the one hand, the oxidation dyestuff precursors of the para type, chosen from diamines or aminophenols in which the functional groups are located in the para-position relative to one another, and, on the other hand, the oxidation dyestuff precursors of the ortho type, and modifying compounds or couplers, which are generally so-called "meta" derivatives chosen more particularly from meta-diamines, meta-amino-phenols, meta-diphenols and also phenols.

The term "rapid oxidation dyestuffs" refers to dyestuff precursors of the benzene series, which contain, on the nucleus, three substitutents chosen from hydroxyl, methoxy and amino groups, and which are capable of oxidising directly in the air.

The term "oxidisable dyestuffs" is used hereafter to denote these various types of dyestuff precursors.

In the semi-permanent dyeing processes using direct dyestuffs, a solution or a dispersion of these dyestuffs is simply applied to the head of hair.

The term "direct dyestuffs" is to be understood as meaning compounds which are coloured in themselves; they belong more particularly to the following classes: nitrobenzene derivatives, azo dyestuffs, anthraquinone dyestuffs, indophenols, indoanilines and indamines.

Attempts have been made for a long time to find means which make it possible to prevent or limit the contact of the scalp with the products used in the dyeing compositions, and especially with the direct dyestuffs or dyestuff precursors as well as the intermediates and final products resulting from oxidative condensation.

It is generally acknowledged that the amounts of products which may penetrate the corneal layer are approximately proportional to the concentration of the products in the dyeing composition. Furthermore, it is acknowledged that part of the products present can subsequently diffuse into the organism.

This possible diffusion, into the body, of the compounds present in the dyeing compositions can present problems of general or specific toxicity. In all cases, it is desirable to be able to protect the scalp against the colouring substances.

We have now discovered, according to the present invention, that powders, suspensions or solutions of substances of vegetable or animal origin, synthetic organic substances or mineral substances or a mixture thereof, which possess a suitable viscosity for application to the hair and possess covering properties, also make it possible to avoid, or at least to limit, the contact of the scalp with the components generally used in oxidation dyeing or in direct dyeing.

We have discovered, in particular, that the use of suspensions of mineral substances possessing adsorbent properties makes it possible to avoid or limit penetration as far as the scalp, of the direct dyestuffs or the components generally used in oxidation dyes.

We have found that the use of these various substances makes it possible to dye the hair over its entire length to give a good uniformity.

The protective effect of the compositions based on these substances can be demonstrated by the absence of stains on the scalp after dyeing in accordance with this process.

Tests carried out on rats show that very low penetration or the absence of penetration of the colouring substances into the epidermis.

This protective effect results totally or partially from the adsorbent properties of the substances, from chemical fixing of the colouring compounds to these substances, from a screening effect and from deactivation of the dyestuff precursors or the coloured products before they reach the scalp. It is self-evident that this theory of the protective effect does not form part of the present invention.

The present invention thus provides a hair dyeing process which consists in applying, in a first stage, at least one composition based on substances of vegetable or animal origin, synthetic organic substances or mineral substances, in suspension or in solution in a solvent, which possess covering properties on the scalp, and have a viscosity suitable for application to the hair, or as a powder and possessing covering properties, and the hair is dyed, in a second stage, using one or more compositions, at least one of which contains an oxidisable and/or direct dyestuff, the dyeing being followed, after an interval sufficient for colouring the hair, by rinsing and then optionally by shampooing.

The solvents which make it possible to suspend or dissolve the covering substances should be cosmetically acceptable solvents, such as water, alcohols, such as ethanol or isopropanol, polyalkylene glycols, such as polyethylene glycol and polyols, such as glycerol or glycols, and mixtures thereof.

The substances used according to the present invention should essentially meet the following criteria when they are in suspension or in solution:

(1) they must cover in such a way as to form an essentially continuous coating, after application;

(2) they must have a sufficient viscosity not to flow during application. It is preferred to use suspensions or solutions of abovementioned substances at a sufficient concentration to obtain a viscosity of 80 to 8,000 cps at 20° C.;

(3) they must be easily removed with water or a shampoo; and (4) the following test must be positive, that is to say that the paper which has been protected by the composition according to the invention must be virtually uncoloured.

This test consists in applying the suspension or solution containing the substance of vegetable or animal origin, the synthetic organic substance or the mineral substance to a white paper (Canson C with a grain of 180 g/m$^2$) to a thickness of 1 mm, the composition being deposited between 1 mm thick wedges. The paper covered in this way is dried at 50° C. for 10 minutes. A conventional oxidation dye having the following composition is then deposited:

Para-phenylenediamine dihydrochloride: 2 g
2,4-Diaminoanisole dihydrochloride: 2.35 g these dyestuffs being dissolved in a carrier comprising:

Oleyl alcohol containing 2 mols of EO: 4.5 g
Oleyl alcohol containing 4 mols of EO: 4.5 g
Ethomeen C$_{25}$ (polyoxyethyleneated coconut amine containing 15 mols of EO): 4.5 g
Diethanolamides of copra fatty acids: 9.0 g
Propylene glycol: 3.6 g
Butoxyglycol: 8.0 g
96° strength ethanol: 5.4 g
35° Be strength sodium bisulphite solution: 1.0 g
22° Be strength ammonia solution: 10.0 g water being added in sufficient amounts to make up to 100 g. (EO=ethylene oxide) 50 g of 20 volume hydrogen peroxide are added to 50 g of this composition. The dyeing composition is applied to the paper prepared as above and the excess dye is removed after an interval of 30 minutes. After this interval, the paper is rubbed with a sponge soaked with shampoo. If the substance can be used for the purposes of the present invention, the paper must be virtually uncoloured.

It is self-evident that the substances selected must also be acceptable from the cosmetic point of view and must be able to be in contact with the skin without adverse effects on the skin.

Amongst the substances of vegetable origin which are more particularly preferred, there may be mentioned active charcoal prepared from vegetable substances such as wood, peat, lignite and seaweed, which are carbonised, and carrageenates, which are essentially sulphate esters of polysaccharides extracted from red marine plants, and in particular from *Chrondus Crispus*. These products essentially contain lambda- and kappa-carrageenate.

Amongst the substances of animal origin, there may be mentioned animal charcoal originating, in particular, from the calcination, in a closed vessel, of animal substances such as bones. The animal charcoal or the active charcoal is preferably used in the form of a suspension in polyethylene glycol. The animal charcoal or the active charcoal can also be used in the form of a powder.

The synthetic organic substances which can be used include in particular, cosmetically acceptable polymers having a molecular weight of 50,000 to 500,000, and in particular salts of polystyrenesulphonic acid and especially the sodium salts sold under the name Flexan, especially Flexan 130 which has a molecular weight of about 100,000. Products of this type are described in French Pat. No. 2,198,729, the disclosure of which is hereby incorporated by reference.

The mineral substances which can be used, are generally, in suspension in water and are generally substances possessing adsorbent properties. These mineral substances in suspension in water are essentially based on alumina, alumino-silicates or aluminium phosphates and meet the four criteria above. The products which are particularly preferred are alumina, aluminium phosphates, and clays such as kaolinites, attapulgites and montmorillonites. The clays which give particularly remarkable results and are used in the preferred embodiment of the invention are the montmorillonites.

In the literature, the term montmorillonite has been used in a general sense to denote either the family or the minerals having the swelling and shrinking properties of this species; it can therefore encompass the trioctahedral types and can be synonymous with smectite and monmorin (Mineralogie des argiles. (Mineralogy of Clays), S. Caillére and S. Hénin, Masson (1963)).

The montmorillonites correspond to the general formula:

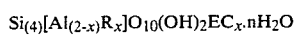

$$Si_{(4)}[Al_{(2-x)}R_x]O_{10}(OH)_2 EC_x \cdot nH_2O$$

EC being an exchangeable cation and R being magnesium, iron or manganese.

The results of the chemical analysis of a series of montmorillonites may be mentioned by way of example.

| | 1 | 2 | 3 | 4 | 5 |
|---|---|---|---|---|---|
| SiO$_2$ | 50.04 | 57.49 | 50.06 | 51.52 | 60.3 |
| Al$_2$O$_3$ | 20.16 | 20.27 | 25.1 | 17.15 | 18.5 |
| Fe$_2$O$_3$ | 0.68 | 2.92 | 0.5 | 5.65 | 0.70 |
| FeO | | 0.19 | | 0.32 | |
| CaO | 1.46 | 0.23 | 4.9 | 1.72 | |
| MgO | 0.23 | 3.18 | 7.2 | 2.80 | 3.8 |
| K$_2$O | 1.27 | 0.28 | | 0.85 | <0.1 |
| Na$_2$O | Traces | 1.32 | | 0.15 | 5.3 |
| TiO$_2$ | | 0.12 | | 0.48 | 0.25 |
| H$_2$O ± | | 6.85 | | 8.55 | |
| | 26.00 | 7.63 | 11.7 | 11.22 | 7.5 |

1 Montmorillonite, Montmorillon (Vienna)
2 Bentonite, Upton, Wyoming (U.S.A.)
3 Montmorillonite, Maharitra (Madagascar)
4 Montmorillonite, Amoy, Mississippi (U.S.A.)
5 Clay sold under the name Gel White USP by Euroclay.

Their large specific surface areas impart valuable properties.

The amount of mineral substances, possessing adsorbent properties, present in the aqueous suspensions or solutions according to the invention is typically 1 to 60% and preferably 5 to 60%.

As mentioned above, the composition used should possess a viscosity which is sufficient for the composition not to flow during application to the hair. For this purpose, products based on mineral substances possessing adsorbent and swelling properties, after introduction into water, are preferably used. Moreover, the substances preferably give thixotropic compositions which are easy to apply because they are fluid after shaking, and which are highly viscous once they have been deposited on the scalp, thus preventing the product from flowing; this is particularly advantageous in the case of the montmorillonites.

These products must also be able to be removed easily with water or shampoo by being resuspended.

A preferred embodiment consists in using white-products so that the user can easily determine whether the entire scalp has been protected suitably. A white product also makes it possible to check that the composition has been removed completely after rinsing.

Another preferred embodiment consists in using, in association with the abovementioned substances and in particular with the mineral substances, a plasticiser, such as polyethylene glycol, which makes it possible to obtain a more uniform film on drying.

It is possible to use mixture of the abovementioned substances and, in particular, to associate up to 1% by weight of active charcoal with the clays. The products which give particularly satisfactory results in this case are based on clay, preferably the montmorillonites.

These compositions based on mineral substances make it possible, in particular, to protect the scalp from the direct dyestuffs, which are preferably used with thickeners, such as cellulose derivatives.

The preferred compounds mentioned above are examplary only; those skilled in the art will be able to find other substances which can be used according to the invention, insofar as they meet the criteria defined above, in particular as regards viscosity, covering properties and removal with water or a shampoo, and the test with the paper.

The amount of substances of vegetable or animal origin, synthetic organic substances or mineral substances, possessing covering properties, which can be used in the suspensions or solutions used according to the present invention is typically 1 to 60%.

In addition to the covering properties, the viscosity and the removal properties mentioned above, the products used according to the invention should enable the dyestuff to penetrate the hair, so that the root of the hair can be dyed.

Once the composition has been applied to the scalp, it is preferably dried by the customary means used in hairdressing salons, for example under a hood.

The dyeing processes used after this first treatment are processes which are in themselves well known and which can be carried out in one or more stages; they can use very diverse compositions which are well known in the art.

Thus, after treatment of the scalp with the composition as defined above, it is possible to apply either a composition containing at least one dyestuff precursor of the ortho or para type, or mixtures thereof, and to develop the colouration with an oxidising agent which is present in the composition applied in the second stage of the process according to the invention, or which is applied to the hair in a third stage, and optionally direct dyestuffs, or a composition containing at least one direct dyestuff.

Amongst the dyestuff precursors of the para type, there may be mentioned, more particularly, the compounds corresponding to the formula:

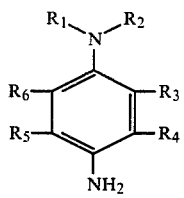

(I)

in which: $R_1$ and $R_2$ independently of one another denote hydrogen, phenyl, furfuryl, tetrahydrofurfuryl or a linear or branched alkyl group which can contain terminal substituents, such as hydroxyl, alkoxy, amino (it being possible for the amine group to be primary, secondary or tertiary or to form part of a heterocyclic ring, such as piperidino or morpholino), acylamino, alkyl- or arylsulphonylamino, carbalkoxyamino, ureido, carboxyl, carbamyl (in which the nitrogen atom can carry one or two substituents), sulpho or sulphonamido (in which the nitrogen atom can carry one or two substituents), it being possible for this alkyl group to contain one or more chain hetero-atoms, such as oxygen and nitrogen, and to carry other hydroxyl or amine groups; $R_1$ and $R_2$ can also form, together with the nitrogen atom to which they are attached, a heterocyclic ring, such as piperidino or morpholino; and $R_3$, $R_4$, $R_5$ and $R_6$ independently of one another denote hydrogen, halogen, linear or branched alkyl optionally substituted by one or more OH, amino or alkoxy groups, or denote a group OZ, Z denoting alkyl, hydroxyalkyl, alkoxyalkyl, acylaminoalkyl, carbalkoxyaminoalkyl, mesylaminoalkyl, ureidoalkyl, aminoalkyl or monoalkyl- or dialkyl-aminoalkyl, the alkyl radicals containing 1 to 6 carbon atoms, with the proviso that if $R_2$ denotes phenyl, $R_1$, $R_3$, $R_4$, $R_5$ and $R_6$ denote hydrogen, and that if $R_1$ and $R_2$ are both other than hydrogen, $R_3$ and $R_6$ denote hydrogen, and also the organic or inorganic acid salts of these bases, such as the hydrobromide, hydrochloride, sulphate, acetate, and tartrate.

Other oxidation dyestuff precursors of the "para" type which can be used according to the invention include para-aminophenols, heterocyclic precursors derived from pyridine, from benzomorpholine and from indole, and bis-condensed precursors, such as N,N'-diarylalkylenediamines in which the aryl groups are substituted in the para-position by an OH or amino group optionally substituted by an alkyl group, and which can be substituted on the nucleus by an alkyl radical or a halogen atom, and in which the alkylene group can contain a chain hetero-atom, such as O or N, and can be optionally substituted by OH or an alkyl group, it being possible for the nitrogen atoms joined to the alkylene group to be substituted by an alkyl, hydroxyalkyl or aminoalkyl group.

Compounds of this type are described, inter alia, in French Pat. No. 2,016,123 (hereby incorporated by reference).

These compositions can also contain oxidation dyestuff precursors of the ortho type, such as ortho-phenylenediamines, ortho-aminophenols and ortho-dihydroxybenzenes or their derivatives substituted on the nitrogen atom by an alkyl or hydroxyalkyl group or substituted on the nucleus by one or more alkyl or alkoxy groups.

The compositions containing the dyestuff precursors of the ortho or para type can also contain modifiers or couplers which are well known in the state of the art. These couplers can also be applied to the hair either before application of the composition containing the dyestuff precursors of the para or ortho type, or after application of the composition containing the said precursors. In that case, the oxidising agent can be present either in the composition applied in the second stage, or in a composition applied in a third stage.

The couplers which can be used more particularly in the process according to the invention include monophenol derivatives, meta-dihydroxybenzenes, meta-aminophenols, meta-diamines, heterocyclic compounds derived from pyridine or from morpholine, pyrazolones or diketone compounds and their salts.

The diphenylamines which can be used in the process according to the invention are diphenylamines in which the two nuclei are substituted in the 4- and 4'-positions by two groups, such as hydroxyl and/or N(R')(R''), in which R' and R'' independently or simultaneously denote hydrogen, alkyl or hydroxyalkyl, and R'' can also denote carbamylalkyl, mesylaminoalkyl, acylaminoalkyl, sulphoalkyl, piperidinoalkyl or morpholinoalkyl, if R' denotes H or alkyl. The radicals R' and R" can also form, together with the nitrogen atom to which they are attached, a piperidine or morpholine ring. The other positions of the two benzene nuclei can be occupied by one or more groups, such as alkyl or alkoxy, it being possible for the alkyl radical to form a heterocyclic ring with a primary or secondary amine group in the 4- or 4'-position, a halogen atom, a ureido radical or amino optionally substituted by a hydroxyalkyl, carbamylalkyl, mesylaminoalkyl, acyl or carbalkoxy group.

These diphenylamines can be used in the form of their salts, such as the sulphate, hydrobromide, hydrochloride, acetate or tartrate.

These diphenylamines are described in French Pat. Nos. 1,222,700, 2,056,799, 2,174,473, 2,145,724, 2,262,023, 2,262,024 and 2,261,750 and Application No. 75/05,503, the disclosure of where are hereby incorporated by reference.

These diphenylamines can be used either in compositions containing the dyestuff precursors of the para or ortho type, or in compositions containing the oxidising agent or the modifiers, or in both compositions.

It is also possible, in the second stage, to dye the hair using compositions containing so-called "rapid" oxidation dyestuffs which are capable of developing simply by contact with the air. Compositions of this type can contain, in particular, dyestuffs chosen from amongst polyhydroxybenzenes and polyhydroxynaphthalenes, polyaminobenzenes, polyaminophenols, polyaminopolyhydroxybenzenes in which the amino groups are optionally substituted by an alkyl radical, and polyhydroxy- and polyaminohydroxy-indoles.

In the formulae of the abovementioned oxidisable dyestuffs, the alkyl groups preferably denote groups having 1 to 6 carbon atoms, alkoxy denotes a group preferably having 1 to 6 carbon atoms, acyl denotes a group having 2 to 7 carbon atoms, halogen preferably denotes chlorine, bromine or fluorine, and the substituents on the nitrogen atom are preferably alkyl groups having 1 to 6 carbon atoms.

The dyeing compositions for permanent colouration which can be used in the process according to the invention can also contain the intermediates or the final products resulting from the oxidative condensation, and direct dyestuffs. More particularly, we have noted that the application, in a first stage, of the composition based on substances of vegetable or animal origin or synthetic organic substances, possessing covering properties, according to the invention, makes it possible, in particular, to prevent the formation of the so-called Bandrowski bases which can result from the condensation of para-phenylenediamines with themselves. We have noted in particular that the formation of the Bandrowski base can be prevented to the extent of up to 90% by weight using these compositions.

The dyeing compositions for semi-permanent colouration which can be used in the process according to the invention essentially contain direct dyestuffs in a cosmetically acceptable medium.

The direct dyestuffs which can be used are well known and are generally nitrobenzenes, azo dyestuffs, anthraquinone dyestuffs, indophenols, indamines or indoanilines, and have the common characteristic of imparting their own colouration to the hair.

The nitrobenzene derivatives which are preferably used are nitrophenylenediamines, nitroaminobenzenes, dinitroaminobenzenes and nitroaminophenols and derivatives thereof, as described in French Patent Application No. 2,290,186, and also nitrodiphenylamines.

The dyeing compositions for permanent colouration suitably have a pH of 8 to 11.5. The dyeing compositions for semi-permanent colouration suitably have a pH of 3 to 11.5.

The dyeing compositions which can be used in the process according to the invention can also contain anionic, cationic, non-ionic or amphoteric surface-active agent, or mixtures thereof, which are well known in the art. The surface-active products are suitably present in the dyeing compositions used according to the invention in an amount from 0.5 to 55% by weight, and preferably from 4 to 40% by weight, relative to the total weight of the composition.

These compositions can also contain organic solvents for solubilising compounds which would not otherwise be sufficiently water-soluble. These solvents are preferably present in an amount from 1 to 40% by weight, and more particularly from 5 to 30% by weight, relative to the total weight of the composition.

Of course, it is possible to add, to the dyeing compositions, any other adjuvant normally used in hair-dyeing compositions, and, in particular, sequestering agents, film-forming agents, buffers, thickeners, anti-oxidants and perfumes.

The presence of thickeners is particularly desired in the case of semi-permanent dyeing compositions, insofar as the protective effect of the composition applied in the first stage is enhanced by the presence of these substances, in particular by the presence of cellulose derivatives, such as carboxymethylcellulose or carboxyethylcellulose, polyacrylic acid derivatives, bentonite, sodium alginate or gum arabic.

The dyeing compositions used can be presented in various forms, such as a liquid, a cream or a gel, or in any other from suitable for dyeing the hair.

They can also be packaged in aerosol flasks, in the presence of a propellant.

If the composition contains an oxidising agent, the latter is suitable hydrogen peroxide or urea peroxide. A solution of hydrogen peroxide of 20 volumes strength is preferably used.

The application of the dyestuffs to the hair should be followed by a sufficient interval to permit colouration. This interval is generally 10 to 40 minutes.

After colouration, the hair is rinsed thoroughly so that all the composition applied in the first stage is also removed, and it is optionally shampooed, rinsed again and then dried.

The following Examples further illustrate the present invention. Where this is not stated the protecting compositions pass the "paper" test.

EXAMPLE 1

A liquid dyeing composition is prepared by mixing the following components:
Nonylphenol containing 9 mols of ethylene oxide: 3 g
Oleyl alcohol: 9 g
Lauryl diethanolamide: 11.5 g
Oleic acid: 18 g
Propylene glycol: 9 g
Benzyl alcohol: 11 g
22° Bé strength ammonia solution: 14 ml
Monoethanolamine: 6.5 g
p-Aminophenol: 0.2 g
m-Diaminoanisole sulphate: 0.1 g Resorcinol: 0.5 g
m-Aminophenol: 0.2 g
p-Toluylenediamine: 2 g
Ethylenediaminetetraacetic acid sold under the name Trilon B: 3 g
Sodium bisulphite solution (d=1.32): 1.2 g
Water q.s.p.: 100 g 30 g of this composition are mixed, in a bowl, with 30 g of hydrogen peroxide of 20 volumes strength.

A 35% strength aqueous suspension of a sodium polystyrenesulphonate marketed by National Starch under the name FLEXAN 130 is applied to a white paper (Canson C with a grain of 180 g/m$^2$).

The paper is then dried at 50° C. for 10 minutes. The oxidation dye described above is then deposited.

After the usual interval (30 minutes), the excess dye is removed and the paper is rubbed with a sponge soaked with shampoo.

It is found that the paper has been protected.

The Flexan 130 composition, packaged in a polyethylene flask incorporating an applicator, is applied to the hair by squeezing the flask. The composition is deposited in the form of lines in accordance with the conventional technique commonly used by hairdressers. After drying under a hood, dyeing is carried out by applying the composition described above. After an interval of 30 minutes, the hair is rinsed, shampooed, rinsed and dried. The head of hair is coloured deep chestnut and the scalp has been well protected.

EXAMPLE 2

Following the procedure described in Example 1, the dyeing composition is deposited on a paper covered with a 30% strength suspension, in polyethylene glycol of molecular weight 400, of animal charcoal containing 15% of ash, marketed by PROLABO. Good protection of the paper and of the scalp is again found on using the process of Example 1.

EXAMPLE 3

A dyeing composition in the form of a liquid is prepared by mixing the following ingredients: Triethanolamine lauryl-sulphate containing
  40% of active ingredient: 4 g
2-Octyldodecanol marketed under the name EUTANOL G by HENKEL: 11 g
Lauryl diethanolamide: 8 g
Nonylphenol containing 9 mols of ethylene oxide: 3 g
Oleic acid: 21 g
Benzyl alcohol: 12 g
96° strength ethyl alcohol: 8 g
22° Bé strength ammonia solution: 19 ml
p-Aminophenol: 0.30 g
Resorcinol: 0.65 g
m-Aminophenol: 0.65 g
p-Toluylenediamine: 0.15 g
Ethylenediaminetetraacetic acid sold under the name Trilon B: 3 g
Sodium bisulphite solution (d=1.32): 1.2 g
Water q.s.p.: 100 g 30 g of this composition are mixed, in a bowl, with 30 g of hydrogen peroxide of 20 volumes strength.

The procedure of Example 1 is followed, this dyeing composition being deposited on a paper covered with an aqueous gel containing 3.3% of carrageenate marketed by SATIA under the name SATIAGEL GS 350. After the usual interval (30 minutes), and shampooing, it can be seen that the paper has been correctly protected.

On applying this composition to the hair as indicated in Example 1, a golden light blond colouration is observed; no stains on the scalp are observed.

EXAMPLE 4

The dye prepared in Example 3 is applied to a paper covered with a 30% strength suspension, in polyethylene glycol of molecular weight 400, of an activated vegetable charcoal marketed by PROLABO, which is finely ground. After washing and drying, the paper has been effectively protected.

EXAMPLE 5

The following dyeing composition for semi-permanent colouration is prepared:
2-Nitro-4-aminophenoxyethanol hydrochloride: 2 g
1-Amino-2-nitro-4-methylaminobenzene: 0.5 g
Carboxymethylcellulose: 5 g
22° Bé strength ammonia solution q.s.p.: pH 10
Water q.s.p.: 100 g This composition is applied to various Canson papers respectively protected by the composition described in Examples 1 to 4 and dried at 50° C. for 10 minutes, and to unprotected samples of paper.

After an interval of 20 minutes, shampooing and drying, it is found that the unprotected control samples have a coppery-red colouration, whereas the papers covered with various compositions have been well protected.

On dyeing the protected hair as indicated in Example 1, no stains on the scalp are observed.

EXAMPLE 6

A composition based on clay is prepared by slowly introducing 10 g of the clay sold under the name Gelwhite into 90 g of softened water containing 0.3 g of a preservative, whilst stirring thoroughly. The suspension is very viscous and thixotropic.

This composition is applied to the scalp under the conditions described in Example 1.

After drying under a hood at 50° C. for 10 minutes, the hair is dyed in accordance with the usual semi-permanent colouration method, using the composition described in Example 5.

After application to the hair, followed by an interval of 30 minutes, the hair is rinsed, shampooed, rinsed and dried.

It is found that the layer based on clay has protected the scalp well, the scalp being unstained, and the hair is dyed uniformly.

EXAMPLE 7

A composition based on clay is prepared by slowly introducing 10 g of the clay sold under the name GELWHITE into 90 g of softened water in which 0.3 g of a preservative has been dissolved beforehand, whilst stirring thoroughly. The suspension thus obtained is very viscous and thixotropic.

This composition, packaged in a polyethylene flask incorporating an applicator, is applied to the hair by squeezing the flask. The composition is deposited in the form of stripes in accordance with the technique commonly used by hairdressers. After drying under a hood at 50° C. for 10 minutes, the hair is dyed in accordance with the usual method.

The following dyeing composition is applied for this purpose:

| | |
|---|---|
| Para-phenylenediamine dihydrochloride | 0.67 g |
| N—β-Hydroxyethyl-para-phenylenediamine sulphate | 0.67 g |
| N,N—Di-(β-hydroxyethyl)-para-phenylenediamine dihydrochloride | 0.67 g |
| Resorcinol | 0.67 g |
| Meta-aminophenol | 0.67 g |
| 2,4-Diaminoanisole | 0.67 g |
| | 4.02 g |

These dyestuffs are dissolved in the following carrier:

Carrier 1

Remcopal 334 (nonylphenol containing 4 mols of ethylene oxide): 8 g
Remcopal 349 (nonylphenol containing 9 mols of ethylene oxide): 8 g
Propylene glycol: 20 g The pH of the composition is adjusted to 10 with 22° Bé strength ammonia solution, and water is added in sufficient amounts to make up to 100 g.

Hydrogen peroxide of 20 volumes strength (50 g) is added to part of this composition (50 g). After application of the dyeing composition to the hair, followed by an interval of 30 minutes, the hair is rinsed, shampooed and rinsed a second time.

It is found that the protective layer based on clay is easily removed and that the scalp has been effectively protected, the scalp being unstained.

EXAMPLE 8

The procedure described in Example 7 is followed, a viscous suspension of clay, prepared by suspending, in 60 g of softened water, 40 g of a superfine green clay sold by Argiletz, being applied in the first stage, and the carrier having the following composition being used in place of the carrier 1 of the dyeing composition:

Carrier 2

Oleyl alcohol containing 2 mols of ethylene oxide: 4.5 g
Oleyl alcohol containing 4 mols of ethylene oxide: 4.5 g
Ethomeen $C_{25}$: 4.5 g
Diethanolamides of copra fatty acids: 9 g
Propylene glycol: 3.6 g
Butylglycol: 8 g
96° strength ethanol: 5.4 g
35° Bé strength sodium bisulphite solution: 1 g
22° Be strength ammonia solution: 10 g
water being added in amounts sufficient to make up to 100 g. The pH of these compositions is 10.2. As in Example 7, effective protection of the scalp is observed together with the absence of stains.

EXAMPLE 9

The procedure described in Example 7 is followed, the following dyeing composition being used to dye the hair:

| | |
|---|---|
| Para-phenylenediamine dihydrochloride | 1 g |
| Para-aminophenol | 1 g |
| Resorcinol | 0.67 g |
| α-Naphthol | 0.67 g |
| 6-Hydroxybenzomorpholine | 0.67 g |
| | 4.01 g |

These dyestuffs are dissolved in the carrier 1 mentioned above. Exactly as in Example 7, it is found that the scalp is effectively protected from the dyestuffs present in the dyeing composition.

EXAMPLE 10

The process is carried out under the same conditions as those described in Example 8, the only difference being that the dyeing composition of Example 9 is used with the carrier no. 2 defined above. Exactly as before, good protection of the scalp is observed.

EXAMPLE 11

The process is carried out under the same conditions as those described in Example 7, the hair being dyed with the following dyeing composition:

| | |
|---|---|
| N—β-Hydroxyethyl-para-phenylenediamine sulphate | 0.67 g |
| N,N—Di-(β-hydroxyethyl)-para-phenylenediamine dihydrochloride | 0.83 g |
| 2,4'-Diamino-5-methyl-4-hydroxydiphenylamine dihydrochloride | 0.3 g |
| Resorcinol | 0.67 g |
| Meta-aminophenol | 0.67 g |
| 2,4-Diaminoanisole | 0.67 g |
| | 3.81 g |

These dyestuffs are dissolved in the carrier 1. After application, followed by an interval, rinsing, shampooing and rinsing again, it is found, exactly as in the preceding examples, that the scalp has been effectively protected.

EXAMPLE 12

Following the procedure described in Example 8, but using the dyeing composition of Example 11 with the carrier 2, it is found that the scalp is also well protected by means of the composition of Example 8.

EXAMPLE 13

A 15% strength suspension of kaolinite in water is first applied to the hair in accordance with the technique described in Example 7. After drying under the conditions described in Example 7, the dyeing composition described in Example 7 above is applied to the hair. After rinsing, shampooing and rinsing again, it can be observed that the composition based on kaolinite has limited the passage of the dyestuffs to the scalp.

EXAMPLE 14

The aqueous suspension containing the clay Gelwhite, prepared as described in Example 7, is applied to a white paper (Canson C with a grain of 180 g/m$^2$) to a thickness of 1 mm, the deposited composition being levelled off between 1 mm thick wedges. The paper covered with clay is dried at 50° C. for 10 minutes. An oxidation dye having the same composition as that described in Example 9 is then deposited. After the usual interval (30 minutes), the excess dye is removed and it is found that the layer of clay deposited on the paper is very brown in colour. The paper is rubbed with a sponge soaked with shampoo and the layer of clay is easily removed. It is found that the paper has been protected; it is virtually uncoloured.

EXAMPLE 15

A 20% strength suspension of attapulgite in water is applied to the hair in accordance with the technique described in Example 7. After drying, the dyeing composition described in Example 7 is applied. After an interval of 30 minutes at ambient temperature, the hair is rinsed, shampooed, rinsed a second time and dried. The protecting composition is easily removed and it is found that the application of the layer of clay has limited the passage of the dyestuffs towards the scalp.

EXAMPLE 16

A 20% strength suspension of attapulgite in water is applied to the hair in accordance with the technique described in Example 7. After drying, the dyeing composition used in the process described in Example 11 is applied. After shampooing, it is found that the composition applied beforehand protects the scalp well.

EXAMPLE 17

A slurry containing 55% of colloidal aluminium phosphate in water is prepared.

This composition is applied to the hair, the hair is dried and dyeing is then carried out, following the procedure described in Example 7, with the dyeing composition described in Example 7.

It is found that the composition applied in the first stage limits the passage of the dyestuffs which are present, or which have been formed, towards the scalp.

EXAMPLE 18

A 25% strength suspension, in water, of the alumina sold under the name Alumine qualité métallographie, finesse 48 heures (metallographic-grade alumina, sedimentation time 48 hours) by DURMAX is prepared.

On following the procedure described in Example 11, it is again found that the composition applied to the hair in the first stage limits the passage, towards the scalp, of the dyestuffs present in the composition and of the products formed during the oxidation.

EXAMPLE 19

A composition based on clay is prepared by dissolving 1 g of polyethylene glycol 400 in 89 g of water and then introducing 12 g of the clay Gelwhite, whilst stirring.

The procedure described in Example 7 is followed, the dyeing composition described in Example 7 or in Example 11 being used.

The existence of a uniform layer of plasticised clay, which is easily removed on washing, is observed together with the absence of stains on the scalp.

EXAMPLE 20

On adding 0.07 g of the activated vegetable charcoal used in Example 4 to the composition of Example 7, and otherwise following the same procedure as described in Example 7, effective protection of the scalp against the dyestuffs used is observed.

We claim:

1. A composition suitable for protecting the skin from contact with dyestuffs and/or dyestuff precursors during the dyeing of human living hair which comprises at least one member selected from the group consisting of charcoal, carrageenate, a cosmetically acceptable polymer derived from polystyrene sulphonic acid having a molecular weight of 50,000 to 500,000, alumina, alumino-silicate or aluminum phosphate or mixtures thereof in suspension or in solution in water, ethanol, isopropanol, polyethylene glycol, glycerol or their mixtures; and polyethylene glycol as a plasticizer, said composition having a viscosity of 80 to 8,000 cps suitable for application on the scalp, said composition being removable with water or with shampoo and substantially preventing the passage of dyestuffs in a para-phenylene diamine oxidation dyeing composition into a paper when it is applied to a sheet of paper to a thickness of 1 mm.

2. A composition according to claim 1 wherein the substance in the suspension or solution is 1 to 60% by weight.

3. A composition according to claim 1 in which the substance in the suspension or solution is a montmorillonite clay.

* * * * *